(12) United States Patent
Radosz et al.

(10) Patent No.: US 7,994,087 B2
(45) Date of Patent: Aug. 9, 2011

(54) HIGHLY ACTIVE CATALYST FOR ATOM TRANSFER RADICAL POLYMERIZATION

(75) Inventors: Maciej Radosz, Laramie, WY (US); Youqing Shen, Laramie, WY (US); Huadong Tang, Laramie, WY (US)

(73) Assignee: Wyoming Research Products Center, Laramie, WY (US)

( * ) Notice: Subject to any disclaimer, the term of this patent is extended or adjusted under 35 U.S.C. 154(b) by 508 days.

(21) Appl. No.: 11/599,110

(22) Filed: Nov. 14, 2006

(65) Prior Publication Data

US 2007/0129239 A1 Jun. 7, 2007

Related U.S. Application Data

(60) Provisional application No. 60/736,493, filed on Nov. 14, 2005.

(51) Int. Cl.
*B01J 31/00* (2006.01)

(52) U.S. Cl. ................... 502/155; 502/162; 502/167

(58) Field of Classification Search .............. 502/162, 502/167, 155
See application file for complete search history.

(56) References Cited

U.S. PATENT DOCUMENTS 6,538,091 B1* 3/2003 Matyjaszewski et al. . 526/329.7

* cited by examiner

*Primary Examiner* — Robert D. Harlan

(74) *Attorney, Agent, or Firm* — Kent A. Herink; Emily E. Harris

(57) ABSTRACT

A class of catalysts with unusually high activity for polymerizing vinyl monomers such as acrylates, methacrylates and styrene is described. The catalysts consists of a metal halide such as CuBr and $FeBr_2$ ligated with multidentate amine-based ligands, for example N,N,N',N'-tetra[(2-pyridal)methyl]ethylenediamine, and additives. The additives, which are tertiary amine compounds, can greatly increase the catalytic activity. The complex is capable of catalyzing a living polymerization reaction at a concentration of the complex below about 0.1 mol %.

15 Claims, 3 Drawing Sheets

HIGHLY ACTIVE CATALYST FOR ATOM TRANSFER RADICAL POLYMERIZATION

This application claims priority to U.S. Patent Application Ser. No. 60/736,493, filed Nov. 14, 2005.

BACKGROUND OF THE INVENTION

The invention relates generally to polymerization catalysts and, more specifically, to catalysts with high activity for atom transfer radical polymerization.

Atom transfer radical polymerization (ATRP) is a known "living" polymerization technique used to polymerize vinyl monomers for the preparation of polymers and copolymers with predictable molecular weight and well-defined architecture. (Wang, J. S.; Matyjaszewski, K. *J. Am. Chem. Soc.* 1995, 117, 5614; Patten, T. E.; Matyjaszewski, K. *Acc. Chem. Res.* 1999, 32, 895; Matyjaszewski, K.; Xia, *J. Chem. Rev.* 2001, 101, 2921.) However, a high concentration (2000~10,000 ppm relative to monomer) of transition-metal catalysts makes them precipitate with and hence contaminate the polymer product. Thus, the technical challenge for ATRP is how to reduce the residual catalyst in the product. (Matyjaszewski, K.; Xia, *J. Chem. Rev.* 2001, 101, 2921; Shen, Y; Tang, H; Ding, S. Prog. *Polym. Sci.* 2004, 29, 1053.) One approach is to remove the catalyst by post-purification, such as washing, reprecipitation (Kasko, A. M.; Heintz, A. M.; Pugh, C. *Macromolecules* 1998, 31, 256) and adsorption (Matyjaszewski, K.; Pintauer, T.; Gaynor, S. *Macromolecules* 2000, 33, 1476), which has been demonstrated on a bench scale. However, these methods lead to high cost, loss of polymer, and scale-up difficulties.

Another approach is to use liquid-liquid biphasic (Xia, J.; Johnson, T.; Gaynor, S. G.; Matyjaszewski, K.; DeSimone, J. *Macromolecules* 1999, 32, 4802-4805; Carmichael, A. J.; Haddleton, D. M.; Bon, S. A. F.; Seddon, K. R. *Chem. Commun.* 2000, 1237-1238; Sarbu, T.; Matyjaszewski, K. *Macromol. Chem. Phys.* 2001, 202, 3379-3391; Haddleton, D. M.; Jackson, S. G.; Bon, S. A. F. *J. Am. Chem. Soc.* 2000, 122, 1542-1543; Ding, S.; Radosz, M.; Shen, Y. *Macromolecules* 2005, 38, 5921-5928) and solid-supported catalysts. (Kickelbick, G.; Paik, H.-j; Matyjaszewski, K. *Macromolecules* 1999, 32, 2941-2947; Haddleton, D. M.; Kukulj, D.; Radigue, A. P. *Chem. Commun.* 1999, 99; Shen, Y.; Zhu, S.; Zeng, F.; Pelton, R. J. Polym. Sci. Part A: Polym. Chem. 2001, 39, 1051-1059; Shen, Y.; Zhu, S.; Pelton, R. *Macromolecules* 2001, 34, 5812-5818; Hong, S. C.; Matyjaszewski, K. *Macromolecules* 2002, 35, 7592-7605; Hong, S. C.; Neugebauer, D.; Inoue, Y.; Lutz, J. F.; Matyjaszewski, K. *Macromolecules* 2003, 36, 27-35; Honigfort, M. E.; Brittain, W. J. *Macromolecules* 2003, 36, 3111-3114; Nguyen, J. V.; Jones, C. W. *Macromolecules* 2004, 37, 1190-1203; Nguyen, J. V.; Jones, C. W. *J. Cata.* 2005, 232, 276-294) However, these methods lead to lower degree of polymerization control and higher cost. (Shen et al., 2004).

An alternative approach to reducing the catalyst residue in the ATRP product is to increase the catalyst activity and hence decrease its concentration to the point where the catalyst can economically be left in the polymer product, an approach which is common to polyolefin technology. (Hlatky, G. G. *Chem. Rev.* 2000, 100, 1347-1376) Matyjaszewski et al. first reported examples of such highly active catalysts, first CuBr/Me6TREN and later CuBr/Me$_4$TAPH. (Xia, J. and Matyjaszewski, K. *Macromolecules* 1998, 31, 5958; Inoue, Y.; Matyjaszewski, K. *Macromolecules* 2004, 37, 4014-4021) A 10 mol % CuBr/Me$_6$TREN relative to the initiator (Cu/initiator molar ratio Cu/I=0.1) was sufficient to polymerize methyl acrylate (MA) and yielded polymer with low polydispersity. Well-controlled poly(butyl acrylate) was prepared at 5 mol % CuBr/Me$_4$TAPH relative to the initiator. For styrene (St) polymerization, 50 mol % catalyst (Cu/I=0.5) relative to the initiator worked well, but 10 mol % catalyst relative to the initiator resulted in low monomer conversion (20%) and high polymer polydispersity (PDI>1.5). This catalyst did not work for methyl methacrylate (MMA).

Along the same lines, Guan and Smart found that UV irritation substantially increased the catalytic activity of CuCl/bipyridine for MMA polymerization. At 2.1% CuCl/bipyridine relative to the initiator (Cu/I=0.021), 75% MMA conversion was obtained in 16 h. (Guan, Z.; Smart, B. *Macromolecules* 2000, 33, 6904-6906.) More recently, Faucher and Zhu reported that, with 1 mol % catalyst relative to initiator, a heterogeneous catalyst CuBr/HMTETA polymerized MMA at 90° C. to about 50% conversion with PDI of 1.1. At lower catalyst concentration (0.1 mol % vs the initiator), the polymerization control was lost (PDI=6.3). (Faucher, S.; Zhu, S. *Ind. Eng. Chem. Res.* 2005, 44, 677.)

SUMMARY OF THE INVENTION

The invention consists of a class of catalysts with unusually high activity for polymerizing monomers, including specifically methyl acrylate, methyl methacrylate and styrene. The class of catalysts is characterized by complexes of metal halides with a nitrogen-containing ligand. An example of this class of catalysts is a CuBr/N,N,N',N'-tetra[(2-pyridal)methyl]ethylenediamine complex, CuBr/TPEDA for short. The catalyst (halide and ligand) concentration is preferably between 0.01 mol % and 50 mol % of the initiator, and more preferably between 0.1 mol % and 5 mol %. A 1 mol % catalyst relative to initiator is sufficient for the polymerization of the three monomers, methyl acrylate, methyl methacrylate and styrene, producing polymers with well-controlled molecular weights and low polydispersity (PDI=1.15, 1.24 and 1.18 respectively). A living polymerization is also observed at the catalyst concentration as low as 0.1 mol % versus initiator (6~8 ppm copper relative to monomer).

An object of the present invention is to provide a catalyst for living radical polymerization of monomers consisting of a metal halide and nitrogen-containing ligand having an unusually high activity such that unusually low concentrations of the catalyst relative to the initiator are required.

Another object of the invention is to provide a catalyst for atom transfer radical polymerization of monomers consisting of a metal halide and nitrogen-containing ligand having an unusually high activity such that unusually low concentrations of the catalyst relative to the initiator are required.

A further object of the invention is to provide such catalysts wherein the metal is preferably copper or iron and the halide is preferably chlorine or bromine.

Still another object of the invention is to provide such catalysts wherein the ligand is a monodentate, bidentate, tridentate or multidentate nitrogen-containing compound.

Still a further object of the invention is to provide such catalysts that also may include additives that the catalytic activity, and specifically including tertiary amines.

DESCRIPTION OF THE INVENTION

N,N,N',N'-tetra[(2-pyridal)methyl]ethylenediamine (TPEDA) is synthesized according to Scheme 1, and forms a white/yellowish complex with CuBr that can quickly be oxidized (turns green), indicating a low reduction electrochemical potential and hence a high ATRP activity.

Synthesis of TPEDA Ligand:

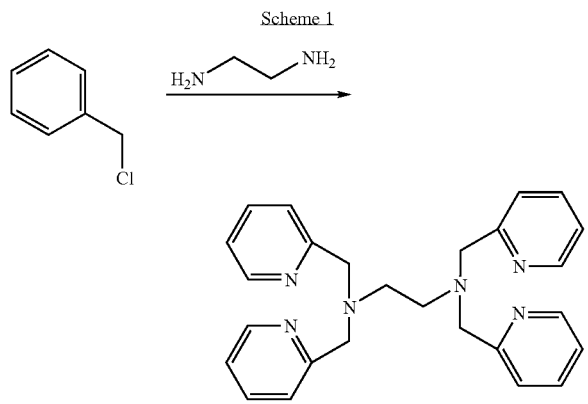

Without being limited thereby, a possible catalyst structure is shown in Scheme 2.

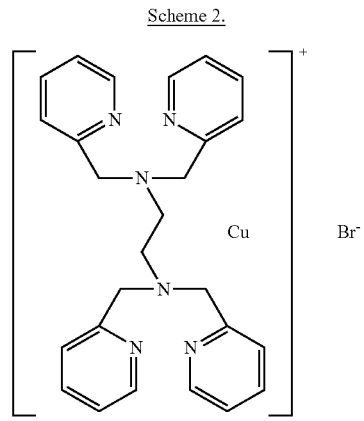

Figure 1:
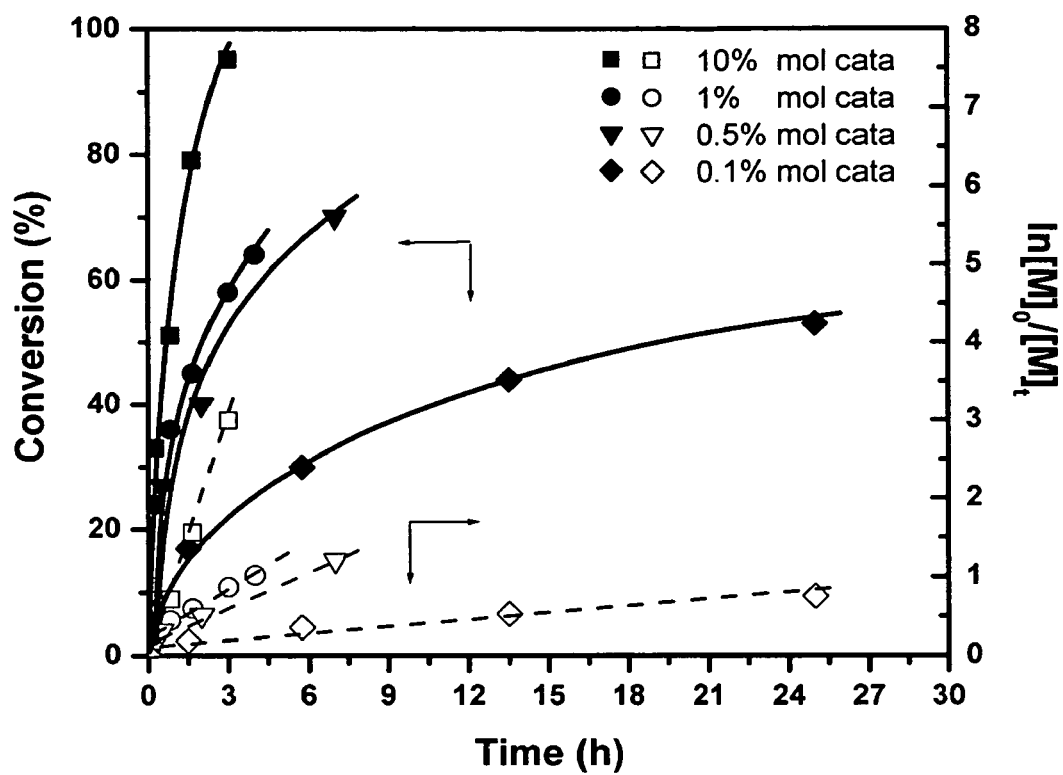
FIG. 1 is a chart of ATRP conversion of MA using CuBr/TPEDA as catalyst. 80° C.; [MA]=10.8 M, [EBiB]=0.108 M, [CuBr]/[TPEDA]=1, [CuBr]=10, 1, 0.5 and 0.1 mol % of [EBiB].
Figure 2:
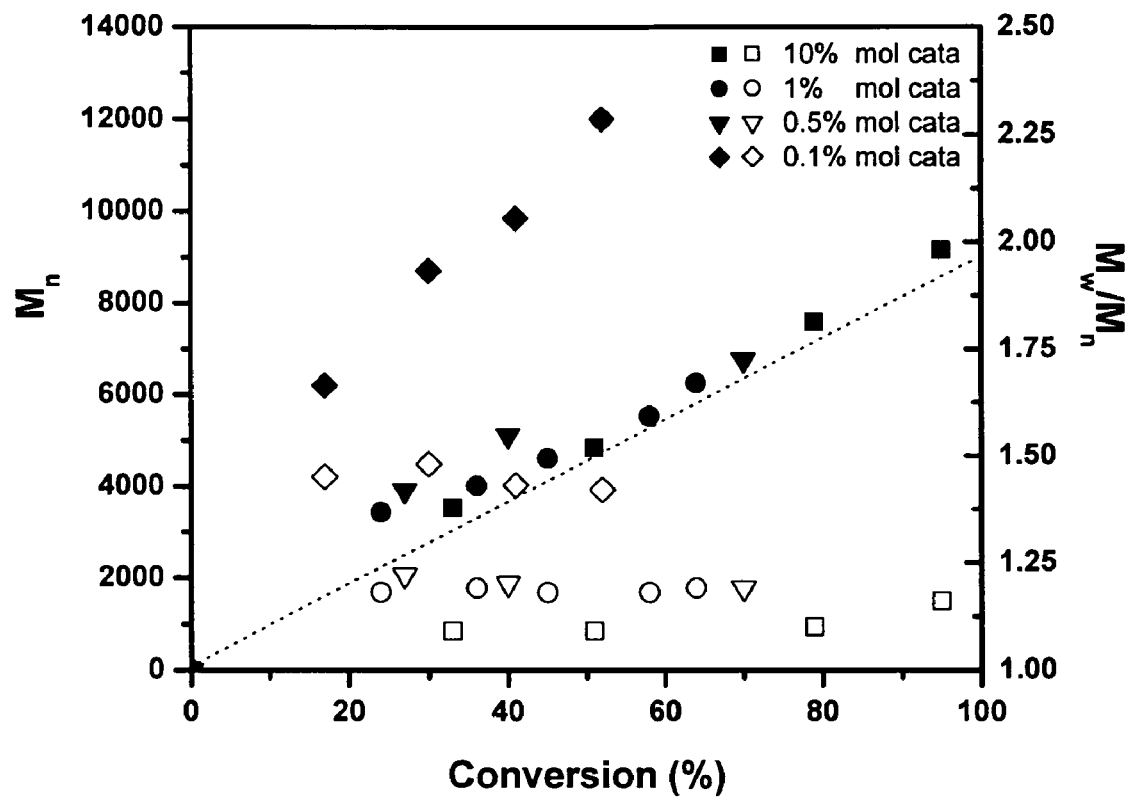
FIG. 2 is a chart of Mn,SEC and Mw/Mn as a function of the ATRP conversion of MA using CuBr/TPEDA as catalyst under the conditions recited regarding FIG. 1.

With ethyl 2-bromoisobutyrate (EBiB) as initiator, 10 mol % CuBr/TPEDA (relative to EBiB) polymerized methyl acrylate (MA) very quickly (80% conversion in 1.5 h) and yielded polymethylacrylate (PMA) with a low polydispersity index (PDI) of 1.15 (FIGS. 1 and 2). At 1 mol % or even 0.5 mol % relative to EBiB, the polymerization was still fast (70% conversion in 7 h at 0.5 mol % catalyst). The ln [M]0/[M] versus time plots of the polymerizations were all linear. The molecular weights of resulting PMA increased linearly with conversion with high initiator efficiency (>90%) and low polydispersity (<1.25).

CuBr/TPEDA catalyzed MA polymerization at concentrations as low as 0.1 mol % relative to EBiB (Cu/I=0.001, or ~7 ppm copper relative to monomer). The PMA molecular weight increased linearly with conversion with PDI of about 1.4. This indicates that the polymerization at such a low catalyst concentration is still a well-controlled living process. The relatively slow polymerization rate and initiator efficiency may be due to side reactions, especially the oxidation by oxygen. At this low catalyst concentration, the radical and the catalyst can be easily oxidized by oxygen. In contrast to CuBr/Me$_6$TREN that was reported to be ineffective for methyl methacrylate (MMA) and styrene, CuBr/TPEDA also showed a very high activity in MMA and styrene polymerizations. Table 1 summarizes the results of ATRP of styrene and MMA using EBiB as initiator. We found that the deactivator CuBr$_2$/TPEDA had relatively low solubility in MMA and styrene and gradually precipitated out during polymerization, which caused slow rate or even prevented polymerization. The addition of a tertiary amine, such triethylamine (TEA) or tributylamine (TBA), was found to dramatically prevent the precipitation of CuBr$_2$/TPEDA and hence improve the polymerization rate. Thus 1 wt % TEA (relative to monomer) was added in MMA polymerization and 1 wt % TBA was added in styrene polymerization.

TABLE 1

ATRP of MMA and styrene using CuBr/TPEDA catalyst

| Entry | [Cu]/[EBiB] | [Cu] (ppm) | time (h) | conv (%) | M$_n$, SEC | M$_n$, Cal | PDI |
|---|---|---|---|---|---|---|---|
| St[a] | 0.01 | 58 | 20.5 | 81 | 6760 | 8420 | 1.18 |
| St[a] | 0.005 | 29 | 25 | 71 | 6600 | 7380 | 1.35 |
| St[a] | 0.001 | 5.8 | 36 | 49 | 5220 | 5090 | 1.66 |
| MMA[b] | 0.01 | 63 | 11.5 | 73 | 12000 | 7300 | 1.24 |
| MMA[b] | 0.001 | 6.3 | 17 | 61 | 30700 | 6100 | 1.34 |
| MMA[b,c] | 0.001 | 7.6 | 25 | 49 | 23000 | 4900 | 1.36 |

[a]1 wt % TBA relative to St, 100° C.
[b]1% wt TEA relative to MMA, 80° C.
[c]with 20 mol % CuBr$_2$ relative to CuBr.

Figure 3:
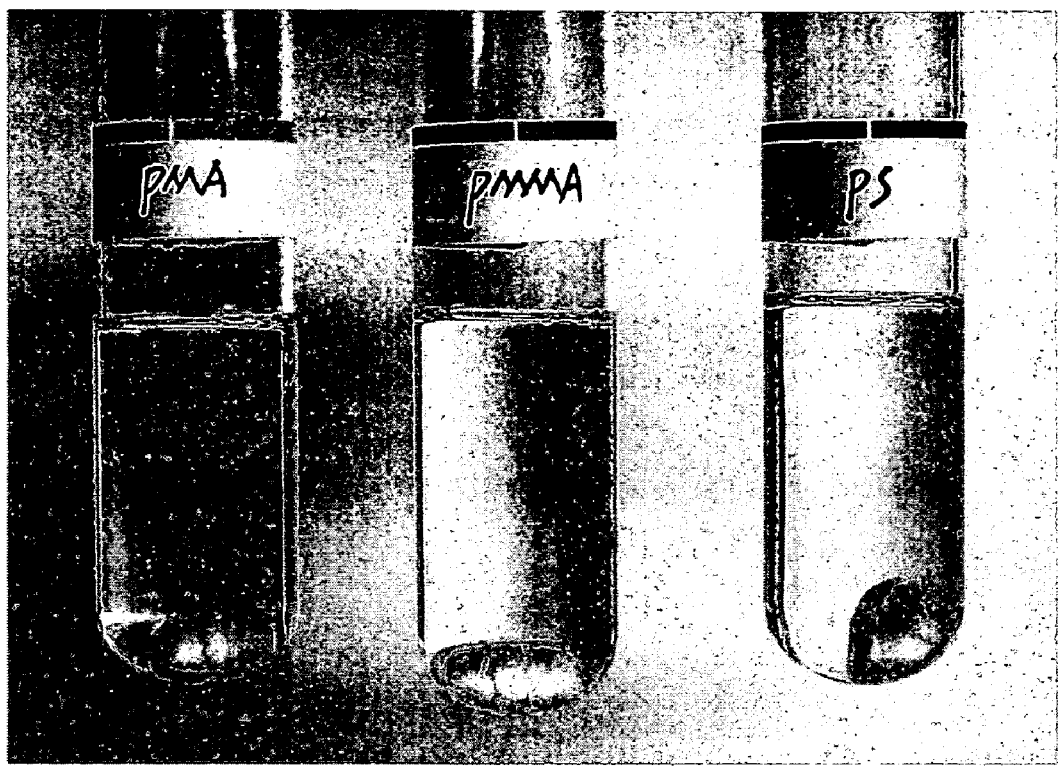
FIG. 3 is a photograph of PMA, PMMA and PS prepared using CuBr/TPEDA catalyst; the residual catalyst concentration is 7.4 ppm copper in PMA, 6.3 ppm in PMMA and 5.8 ppm in PS.

Similar to the MA polymerization, the MMA and styrene polymerization proceeded very well at 1 mol % catalyst to EBiB (Cu/I=0.01), producing polymers with low polydispersity and molecular weights approaching their theoretical limits. A catalyst concentration of 0.5 mol % of EBiB still effectively catalyzed the polymerization of styrene in a well-controlled manner (PDI=1.35). Further decreasing the catalyst concentration to 0.1 mol % relative to EBiB (~6 ppm) slowed the polymerization and resulted in a slightly broader polydispersity (1.66) of polystyrene, but the polystyrene molecular weight was still well controlled. At this low catalyst concentration, CuBr/TPEDA also catalyzed a controlled polymerization of MMA (PMMA PDI=1.37) in spite of the low initiator efficiency. The addition of deactivator CuBr$_2$ only slightly improved the control level. Low initiator efficiency was also reported in MMA polymerization when CuBr/Me$_6$TREN as catalyst. (Queffelec, J.; Gaynor, S. G.; Matyjaszewski, K. *Macromolecules* 2000, 33, 8629.) The major reason is believed to be that the CuBr/TPEDA and CuBr/Me$_6$TREN had too high ATRP equilibrium constant K$_{eq}$ for MMA monomer, which results in fast activation and thus produces a high radical concentration at the early stage of reaction. Irreversible radical termination is significant at high radical concentration, leading to slow polymerization and low initiator efficiency. At catalyst concentrations of 1 mol % of initiator or lower, the resulting polymers were transparent and almost colorless (FIG. 3). The residual copper in the polymers at the catalyst of 0.5 mol % of EBiB is about 30 ppm. One precipitation easily reduces it to several ppm. It is lower than 8 ppm at the catalyst of 0.1 mol % of EBIB. For general industrial use, no post-purification or catalyst recycle is needed, which makes CuBr/TPEDA a very promising catalyst for ATRP commercialization.

In conclusion, a new class of ATRP catalysts comprising a metal halide complex with a nitrogen-containing ligand, and including specifically CuBr/TPEDA, having very high activity for methyl acrylate, methyl methacrylate and styrene polymerizations has been discovered. A 1 mol % catalyst relative to initiator is sufficient for the polymerization of the three monomers, producing polymers with well-controlled molecular weights and low polydispersity (PDI=1.15, 1.24 and 1.18 respectively). A living polymerization could also be achieved at the catalyst concentration as low as 0.1 mol % versus initiator (6~8 ppm copper relative to monomer).

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

We claim:

1. A catalyst for living radical polymerization of one or more monomers, comprising a complex of a metal halide and nitrogen containing ligand that form a bimetal complex having activity at a concentration relative to an initiator between 0.01 mol % and 50 mol %.

2. A catalyst as defined in claim 1, wherein the living radical polymerization comprises atom transfer polymerization.

3. A catalyst as defined in claim 1, wherein said monomers are selected from the group consisting of methyl acrylates, methyl methacrylates, and styrenic monomers.

4. A catalyst as defined in claim 1, wherein the concentration is between 0.1 to 5 mol % of the initiator.

5. A catalyst as defined in claim 1, wherein the ligand is selected from the group consisting of monodentate, bidentate, tridentate and multidentate nitrogen-containing compounds.

6. A catalyst as defined in claim 5, wherein the metal is copper, the halide is bromide and the ligand is N,N,N',N'-tetra[(2-pyridal)methyl]ethylenediamine.

7. A catalyst as defined in claim 1 where the metal is selected from the group consisting of copper, iron, cobalt, and nickel and the halide is selected from the group consisting of chloride and bromide.

8. A catalyst defined in claim 1, further comprising tertiary amines.

9. A catalyst as defined in claim 1, wherein the ligand is N,N,N',N'-tetra[(2-pyridal)methyl]ethylenediamine.

10. A catalyst for atom transfer radical polymerization of one or more monomers, comprising a bimetal complex of metal halide and a nitrogen-containing ligand having activity at a concentration relative to an initiator between 0.001 mol % and 50 mol %.

11. A catalyst as defined in claim 10, wherein the metal is selected from the group consisting of cooper, iron, cobalt, and nickel, preferably cooper, and the halide is selected from group consisting of bromide and chloride.

12. A catalyst as defined in claim 10, wherein the nitrogen-containing ligand is N,N,N',N'-tetra[(2-pyridal)methyl]ethylenediamine.

13. A catalyst as defined in claim 10, where the catalyst concentration is between 0.01 mol % and 50 mol % relative to initiator.

14. A catalyst as defined in claim 10, where the catalyst concentration is between 0.1 mol %~5 mol % of the initiator.

15. A catalyst defined in claim 10, wherein the said monomers are selected from the group consisting of acrylates, methacrylates, and styrenic monomers, preferably methyl acrylate, methyl methacrylate, and styrene

* * * * *